United States Patent [19]

Pike

[11] Patent Number: 4,979,403
[45] Date of Patent: Dec. 25, 1990

[54] PROCEDURE FOR THE QUANTIFICATION OF DUST COLLECTABILITY

[76] Inventor: Daniel E. Pike, 19 Jay St., Harrington Park, N.J. 07649

[21] Appl. No.: 399,627

[22] Filed: Aug. 28, 1989

[51] Int. Cl.$^5$ .......................... G01N 1/22; G01N 5/02
[52] U.S. Cl. ................... 73/863.22; 73/28.05; 73/863.23; 177/50
[58] Field of Search .......... 73/863.22, 863.23, 863.24, 73/863.25, 863.02, 863.03, 865.5, 28, 863.58, 864.73, 864.74, 28.01–28.06; 364/555; 177/50

[56] References Cited

U.S. PATENT DOCUMENTS

| | | | |
|---|---|---|---|
| 2,353,828 | 7/1944 | Hyde | 73/28 X |
| 3,222,925 | 12/1965 | Kracke et al. | 73/28 X |
| 3,457,787 | 7/1969 | Maatsch et al. | 73/863.24 X |
| 3,678,759 | 7/1972 | Schneeberger | 73/28 X |
| 3,698,871 | 10/1972 | Brennan | 73/28 X |
| 3,705,478 | 12/1972 | Vaneldik et al. | 73/863.24 X |
| 3,784,902 | 1/1974 | Huber | 73/28 X |
| 3,787,123 | 1/1974 | Sigrist | 73/28 X |
| 3,795,135 | 3/1974 | Andersen | 73/28 |
| 4,479,379 | 10/1984 | Terry | 73/863.58 X |
| 4,509,727 | 4/1985 | Davis et al. | 73/28 X |

Primary Examiner—Tom Noland
Attorney, Agent, or Firm—Richard A. Joel

[57] ABSTRACT

A method and apparatus for determining the collectability of dust particles is disclosed herein. The concept of collectability and collectivity are employed to establish fundamental equations which are solved by the use of data obtained by passing a dust laden gas through a sampling train having a plurality of impingers. The weight of material collected in each separate impinger is determined and using these individual weights a mathematical matrix is set up from which the collectability of the dust particles is obtained. The collectability of a given dust particle is defined as its impinger efficiency when the impinger is operated in strict accordance with design specifications. Collectivity is defined as the collectability distribution of a mixture of dust particles having different collectabilities.

6 Claims, 2 Drawing Sheets

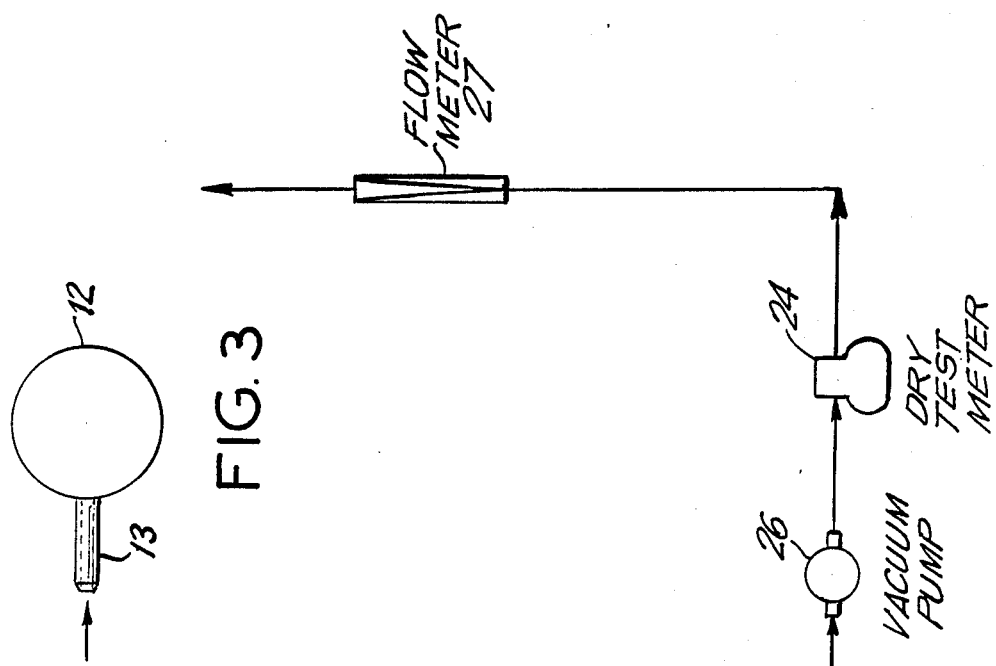
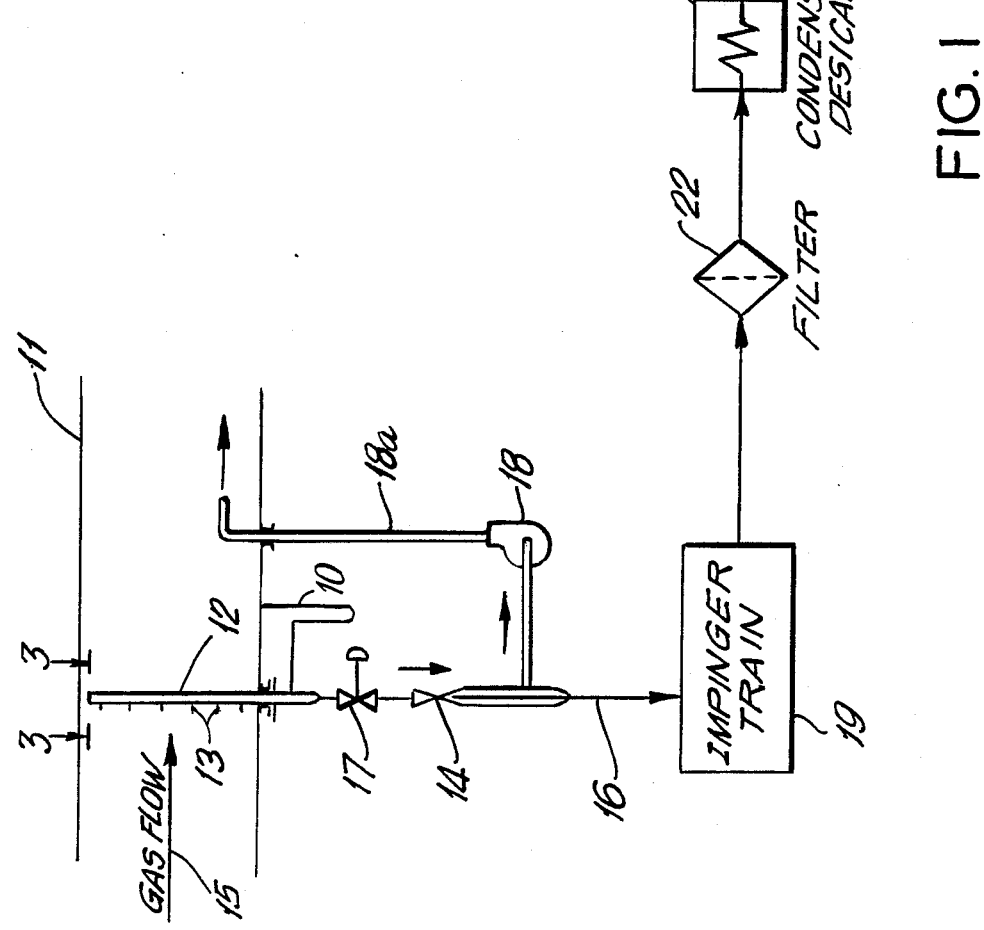

PROCEDURE FOR THE QUANTIFICATION OF DUST COLLECTABILITY

BACKGROUND OF THE INVENTION

One of the problems encountered in the design of pollution control apparatus is the lack of a standard means to predict accurately the gas cleaning efficiency of pollution control devices. For years, pollution control engineers have used particle size as the main criteria in their calculations for gas cleaning efficiency. This was particularly true for Venturi Scrubbers. However, particle size alone does not determine gas cleaning efficiency and using this measure alone is inadequate for practical design work.

The method of this invention accomplishes the above by introducing the new concepts of collectability and collectivity which take into account all of the variables and mechanisms involved in the wet collection process known as impaction. Heretofore, particle size and particle size distribution were the main criteria in design calculations. Particle size alone, however, does not determine gas cleaning efficiency and Venturi pressure drop. Other particle characteristics such as shape, density and electrostatic charge must be taken into consideration. A term called "aerodynamic particle diameter" takes into account shape and density but not electrostatic charge.

The present invention comprises a method and apparatus for accurately quantifying the collectivity of a mixture of dust particles with various collectabilities. Knowing the collectivity of the dust mixture in a dust laden air/gas stream as described in this invention, the following can be accomplished:

1. The collectability of the dust particles will be expressed as positive fractions between zero and one.
2. The collectivity of the dust mixture will be reported in a table or a graph showing weight fraction versus collectability.
3. By determining the collectivity of a dust from a dust generating process, the Venturi pressure drop required for any gas cleaning efficiency or outlet dust concentration can be determined without the necessity of making pilot plant studies.
4. By testing the inlet and the outlet gas streams of a pollution control system, its comparative performance will be known. Knowing the collectivity of the inlet and outlet gas streams, not only the system's actual efficiency on particles of all collectabilities can be calculated but these actual efficiencies can be compared to those efficiencies of all other systems tested in this manner even if the systems are on different applications. Thus, we have a means for comparing gas cleaning systems on boilers, blast furnaces, kilns, incinerators and all other applications.
5. Obviously, liquid entrainment can be determined by the gain of water in the first impinger if other gains/losses are taken into account. But more important, the amount of particulate matter in this liquid entrainment can be determined using the concept of collectability.

Specifically, there is no relevant prior art of record since applicant is disclosing a new concept herein. Consequently, the cited prior art is merely of marginal interest although the invention may lie in the same general field. In prior art, cascade impactors have been used to determine particle size but the present invention relates to collectability as defined herein.

In the prior art, Davis et al U.S. Pat. No. 4,509,727 discloses an off-gas monitor for determining gas scrubber efficiency in steel processes. The method comprises comparing the particulate matter in a gas stream before and after chemical treatment to determine the efficiency of the treatment.

Tarcy U.S. Pat. No. 4,479,379 discloses a method and apparatus for continuous analysis of a gas and particulate stream. A sampling nozzle is placed in a gas and particulate stream and a solvent is injected creating an aerosol which enhances dissolution of gas in the solvent. A continuous analysis means examines the concentration of dissolved gas and particulate.

Also of interest are prior art Vaneldik U.S. Pat. No. 3,705,478 and Maatsck U.S. Pat. No. 3,457,787. The prior art patents show different means for measuring the concentration of particles in a gas and indeed in the environment of pollution control devices such as scrubbers and precipitators. None of the patents discloses the apparatus and method of the present invention.

SUMMARY OF THE INVENTION

The present invention comprises a method and apparatus for quantifying the collectability of dust particles in a gas stream. The method utilizes the concept of "collectability" and "collectivity" to account for all of the variables and mechanisms involved in the wet collection process known as impaction. The apparatus includes a sampling train which comprises an impinger train operating under specific conditions and comprising a plurality of impingers in series which are accurately calibrated with known dusts. The weight of material collected in each separate impinger is determined and using these individual weights a mathematical matrix is set up from which the collectability of the dust particles is obtained. "Collectability" is the efficiency of collection of a given particle in a specially designed and operated impinger while the term collectivity is an expression of the collectabilities of all particles in a dust mixture.

In operation, the particulate laden gas stream is passed through a train of impingers. Knowing the weight of dust collected in each impinger and also the weight passing through the impinger train, the weight fraction of dust in a number of classes (ranges) of collectabilities can be determined.

The number of classes is the number of impingers in the train. In practice 10 impingers and 10 classes have been chosen but any number can be used. A particle with a specific collectability has a specific curve relating gas cleaning efficiency with Venturi pressure drop. Likewise, for an electrostatic precipitator this particle will have a specific curve relating gas cleaning efficiency with voltage, retention time and migration velocity.

Accordingly, it is an object of this invention to provide a new and unique method and apparatus for quantifying the collectability of dust particles in a gas.

A further object of this invention is to provide a new and improved method for measuring the efficiency of air pollution control apparatus.

A still further object of this invention is to provide a new and improved apparatus for measuring the efficiency of air pollution control apparatus.

A more specific object of this invention is to provide a new method and apparatus for determining collectability by passing a dust laden gas through a sampling train having a plurality of impingers so that the weight of dust particles in each impinger can be obtained, and using a mathematical matrix, the efficiency of the impinger on individual particles can be determined. The invention also introduces the concept of collectivity which is defined as the collectability distribution of a mixture of dust particles having different collectabilities.

DESCRIPTION OF THE DRAWINGS

The above and other objects of the invention may be more clearly seen when viewed in conjunction with the accompanying drawings wherein:

FIG. 1 is a schematic diagram of the apparatus for practicing the method of the invention;

FIG. 3 is a crossection view of the probe for sampling the gas stream.

DETAILED DESCRIPTION OF THE INVENTION

Figure 2:
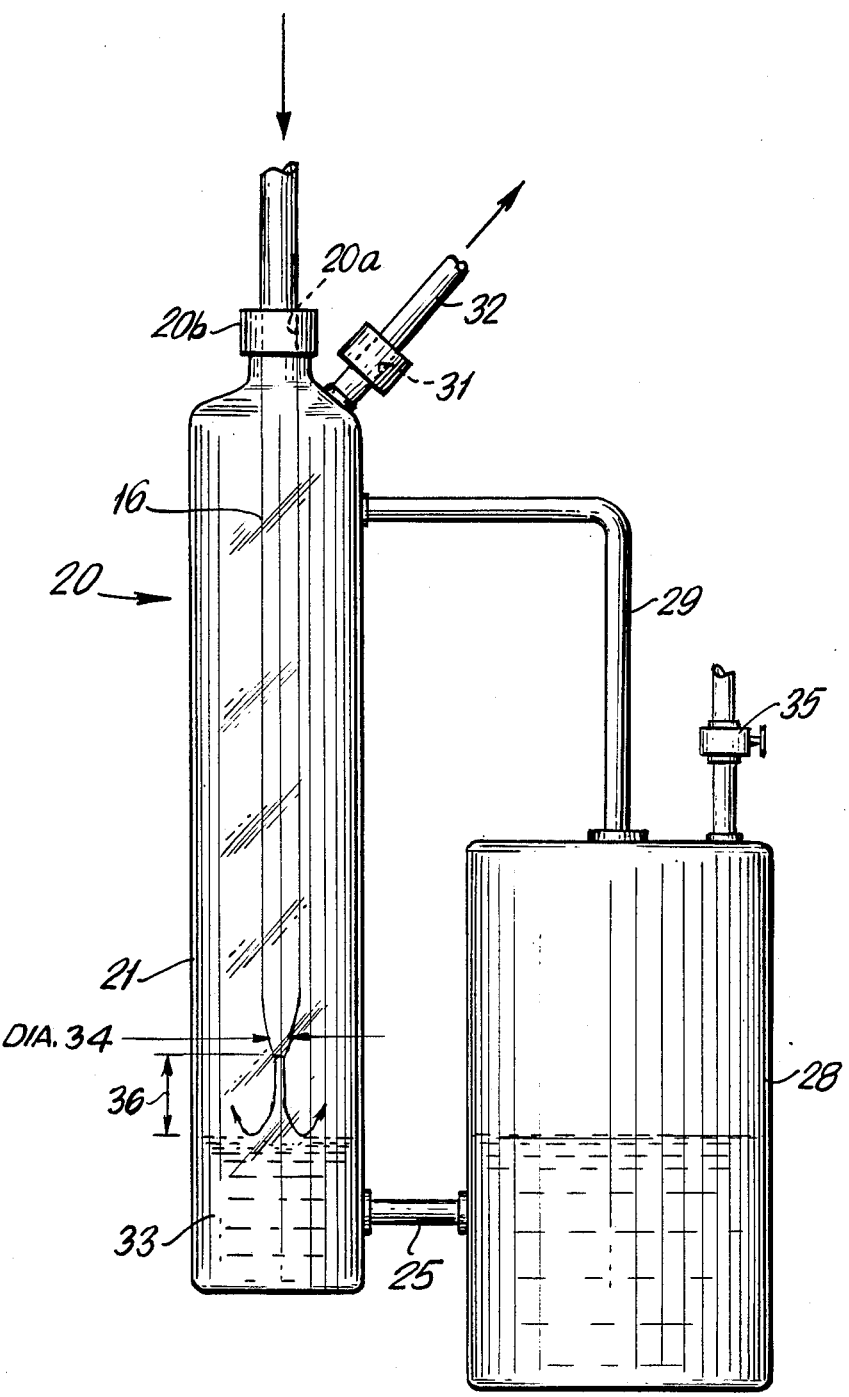
FIG. 2 is a cross-sectional view of a typical impinger in the impinger train.

Referring now to the drawings, the invention comprises a method and apparatus for determining the collectability of dust particles in a gas. Collectability is a dimensionless number between zero and one and it is equal to the efficiency of collection of a given particle in a special impinger. Another concept introduced by this invention is "collectivity" which is an expression of all the collectabilities of a given dust mixture. Collectivity can be expressed in tabular form in which a small range of collectability is given versus weight percent in that range or it can be expressed (as in particle size distribution) as "weight percent less than" a certain collectability or it may be expressed in equation form.

The sampling and testing procedure of this invention was developed to provide the following:

1. Provide information about the characteristics of a dust in addition to the dust concentration from a single dust sample.

2. Provide a direct means of evaluating the relative performance of any gas cleaning system.

3. Provide a means of determining the pressure drop required for any gas cleaning efficiency of a Venturi Scrubber.

4. Provide a sampling procedure in which the sampling probe:
   (a). will not retain a significant portion of the dust and
   (b). will not require movement to several positions in the duct for iso-kinetic sampling.

5. Determine entrainment of scrubbing liquid and particulate matter therein.

As shown in FIG. 1, the sampling train 10 of the present invention comprises a duct 11 through which a dust laden gas stream 15 passes in the indicated direction. The sampling probe 12 includes a minimum of six sampling ports 13. The location of the probe 12 is critical since it is equivalent to a single traverse of a conventional one-port probe.

The probe 12 is coupled to a metering Venturi 14 with an outlet extraction tube 16. A control valve 17 and a blower 18 are also coupled to the Venturi 14 in an arrangement which measures and controls gas flow under iso-kinetic conditions. The flow from the extraction tube 16, also under iso-kinetic conditions from the Venturu 14, passes to an impinger train 19 which in a preferred embodiment comprises ten impingers in series. The flow from the blower 18 is reintroduced to the duct 11 through tube 18a.

The individual impingers 20 (FIG. 2) collect decreasing amounts of dust as the gas stream passes from the first to the last impinger. The stream then passes through a final filter 22 to a cooler-condenser-desicant 23, and a dry test meter 24. A vacuum pump 26 maintains the flow of gas and a flow meter 27 measures that flow.

In the sampling procedure, the metering Venturi 14 and blower 18 are started and adjusted to obtain iso-kinetic sampling conditions in the main duct 11 by maintaining a specified pressure as measured by manometer 10. The Venturi 14 and blower 18 are run for a minimum of one hour before starting the sampling train 19. The gas flow through the metering Venturi is an order of magnitude greater than that through the impinger train 19. After an initial build-up of dust in the probe 12, further dust accumulation ceases and probe dust catch can usually be neglected. Nevertheless, the probe 12 is always washed and the dust accumulation determined after every test. If the accumulation happens to be significant, it can be added to the final result.

After the proper sampling conditions are reached, the impinger train 19 is started and the gas flow adjusted to stated conditions. Sampling can be continued as long as necessary to obtain measurable amounts of contaminants (dust) in the last impinger 20. Since most of the dust is caught in the impingers 20, the final filter 22 is seldom overloaded and need not be changed during the test. While a preferred embodiment would comprise 10 impingers, any number can be used with the results and structure of the train differing.

After the sampling period, the final weight of material collected in each impinger 20 is determined. The total weight of material passing through the impingers 20 is determined by adding the weight of material collected on the filter to the sum of all impinger weights. Since the individual weights are known, the collection efficiency of each impinger 20 can be calculated.

However, overall impinger efficiency is not the same as collectability but having all of these quantities and variables, it is possible to obtain curves (graphs) showing "percent by weight less than" a certain collectability or "percent by weight" in a given range of collectabilities. Any of these curves thus constitute the collectivity of the dust particles.

Testing shows that the material in the clean gas from most pollution control systems contains a large percentage by weight of material with a collectability of one (1.0000). The term "debris" is used to describe this material. It is material that requires no Venturi pressure drop for collection in a Venturi scrubber or no applied voltage in an electrostatic precipitator. In a wet system, it is entrainment or mist which can carry soluble material as well as particulates, both sub-micron and plus-micron. In the present method this material is a major portion of the catch of the first impinger and can be reported separately. The balance of the particulates are then collected in the following impingers and final filter.

A typical impinger 20 is shown in FIG. 2. The impinger 20 comprises a substantially cylindrical container 21 with the extraction tube 16 extending downwardly through an aperture 20a in the cap 20b and being spaced a predetermined distance above the water 33 in the bottom of the container 21. The outlet diameter 34 of the tube 16 and the distance 36 of the tube above the water are two important constants.

The lower portion of the container 21 is connected via tube 25 to the reservoir 28 which includes an upper outlet tube 29 which is connected to the upper portion of the container 21. The water 24 in the reservoir 28 is used to raise or lower the water level in the container 21 in order to maintain the distance of the tube 16 above the water 24. This is done by raising or lowering vessel 28 in relation to container 21 by use of flexible tubing for 25 and 29. The valve 35 is used to supply water to the reservoir 28. Clamps or other controls may be used to control the water level. Typically, the hot or saturated gas enters the impinger 20 through tube 16 and exits through upper opening 31 to the tube 32 and then to the next of the serially connected impingers 20. The weight of the dust collected in the impingers is obtained by filtering the liquid and weighing the material on a filter paper. This is done for each of the impingers and the results fed into a computer programmed with equations to provide the collectivity.

An individual dust particle has a specific collectability which is its efficiency of collection in a standardized dust sampling device, the impinger 20 as described above. On the other hand, collectivity is the knowing or determination of all the combined collectabilities of all of the individual dust particles of a dust mixture. Thus collectability is analogous to individual particle size while collectivity is analogous to particle size distribution.

The sampling device disclosed herein is an impinger 20 with a given fixed jet diameter operated at a fixed pressure drop and a fixed jet impaction parameter which may be represented by the equation:

$$K = \frac{C u \rho D_p^2}{\mu D_j}$$

where:
u = jet velocity
$\rho$ = particle density
$D_p$ = particle diameter
$\mu$ = gas viscosity
$D_j$ = jet diameter
C = Cunningham corrector factor For a sampling train 19 containing, for example a plurality of five impingers, one obtains five equations and five unknowns as follows:

$W_1 = E_a x_a + E_b x_b + E_c x_c + E_d x_d + E_e x_e$ $W_2 = I_a E_a x_a + I_b E_b x_b + I_c E_c x_c + I_d E_d x_d + I_e E_e x_e$ $W_3 = I_a^2 E_a x_a + I_b^2 E_b x_b + I_c^2 E_c x_c + I_d^2 E_d x_d + I_e^2 E_e x_e$ $W_4 = I_a^3 E_a x_a + I_b^3 E_b x_b + I_c^3 E_c x_c + I_d^3 E_d x_d + I_e^3 E_e x_e$ $W_5 = I_a^4 E_a x_a + I_b^4 E_b x_b + I_c^4 E_c x_c + I_d^4 E_d x_d + I_e^4 E_e x_e$ $E_{a1}$, $E_b$, etc. = average collectability of a class of particles, whose individual collectabilities lie in a narrow range, e.g. 0.99 to 1.00 or 0 to 0.01. These ranges can be set arbitrarily but must cover the span 0 to 1.

$W_1$, $W_2$, etc. = weight fraction collected in each impinger $x_a$, $x_b$, etc. = weight fraction of class a,b,etc. particles (collectability distribution or collectivity)
$x_f$ = Weight fraction caught on filter
$I_a = 1 - E_a$, $I_b = 1 - E_b$, $I_c = 1 - E_c$, etc.
Then:

Total wt collected = $W_1 + W_2 + W_3 + W_4 + W_5 + x_f = 1$

Total wt collected = $x_a + x_b + x_c + x_d + x_e + x_f = 1$

This is one way of expressing collectivity.

| | |
|---|---|
| Known quantities: | $W_1, W_2, W_3, W_4, W_5, x_f$ $E_a, E_b, E_c, E_d, E_e$ |
| Unknown quantities: | $x_a, x_b, x_c, x_d, x_e$ |

The unknown quantities are obtained by solving the above five equations. These equations form a matrix which can be solved through the use of determinants. If the range of $E_a$ is set so that it approaches one, e.g. 0.96 to 1.0, the fraction $x_a$ of the dust will have high collectability and will require a low pressure drop for high efficiency of collection in a Venturi Scrubber. If the range of $E_e$ is set so that it approaches zero, e.g. 0–0.04, the fraction $x_e$ will have a much lower collectability and will require a high pressure drop for collection with a reasonable efficiency.

It is understood that the above described arrangements are merely illustrating examples of the invention. Numerous other arrangements may be readily devised by those skilled in the art which will embody the principles of the invention and fall within the spirit and scope thereof.

What is claimed is:

1. The method of quantifying the collectability of dust particles in a gas stream which comprises the steps of:
    passing a dust laden gas through a sampling train having a plurality of impingers,
    collecting the dust particles in each impinger as the gas passes through the impinger train,
    weighing the dust particles collected in each impinger, and setting up mathematical equations using the weights of dust collected in each individual impinger from which the collectability distribution of the dust particles is obtained.

2. The method of claim 1 further including the steps of:
    setting up a mathematical matrix from which the collectivity of the dust particles is obtained.

3. The method of claim 1 further including the steps of:
    obtaining a sample of a gas stream by means of a probe inserted into the gas stream,
    controlling the flow of the gas stream sample under iso-kinetic conditions to the impinger train, and
    filtering the sampled gas from the impinger train to capture any dust which has escaped the impingers.

4. The method of claim 1 wherein:
    the gas is passed through an impinger train wherein the impingers are connected in series.

5. The method of accurately quantifying the collectivity of a mixture of dust particles with various collectabilities comprising the steps of:
    providing a plurality of dust collecting devices in a series-connected sampling train, directing a representative sample of a dust laden gas stream from a main duct to the dust collecting devices,
weighing the dust collected in each device,
setting up a mathematical matrix from which the collectability of the dust particles is obtained, and
determining the collectivity of the dust mixture from the weights of dust collected in each of the devices.

6. The method of claim 5 wherein:
the dust collecting devices comprise a plurality of impingers.

* * * * *